(12) United States Patent
Wakamatsu

(10) Patent No.: US 8,492,360 B2
(45) Date of Patent: Jul. 23, 2013

(54) CREAMY O/W EMULSION COMPOSITION AND PRODUCTION PROCESS THEREOF

(75) Inventor: Kosaburo Wakamatsu, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/995,894

(22) PCT Filed: Jun. 2, 2009

(86) PCT No.: PCT/JP2009/060086
§ 371 (c)(1),
(2), (4) Date: Dec. 2, 2010

(87) PCT Pub. No.: WO2009/148059
PCT Pub. Date: Dec. 10, 2009

(65) Prior Publication Data
US 2011/0112045 A1    May 12, 2011

(30) Foreign Application Priority Data
Jun. 3, 2008  (JP) .................. 2008-146104

(51) Int. Cl.
*A01N 43/04* (2006.01)
*A61K 31/70* (2006.01)
(52) U.S. Cl.
USPC ......................................................... 514/47
(58) Field of Classification Search
None
See application file for complete search history.

(56) References Cited

U.S. PATENT DOCUMENTS

| 2004/0029761 A1 | 2/2004 | Wakamatsu et al. |
| 2005/0220827 A1 | 10/2005 | Tanaka et al. |
| 2009/0285876 A1* | 11/2009 | Hein et al. ................... 424/443 |

FOREIGN PATENT DOCUMENTS

| JP | 55-141174 | 11/1980 |
| JP | 7-126191 | 5/1995 |
| JP | 2002-234830 | 8/2002 |
| JP | 2004-513068 | 4/2004 |

OTHER PUBLICATIONS

NDT glossary, http://www.ndt-ed.org/GeneralResources/Glossary/letter/s.htm, p. 1, obtained from web on Jul. 13, 2012.*
Supplementary European Search Report dated May 25, 2011.
Edited by Nippon Iyakuhin Tenkabutsu Kyokai, Iyakuhin Tenkabutsu Jiten 1st edition, pp. 184, 191, (Jan. 14, 1994).
International Search Report from the Japanese Patent Office in International Application No. PCT/JP2009/060086 mailed Sep. 8, 2009.

* cited by examiner

*Primary Examiner* — Layla Bland
(74) *Attorney, Agent, or Firm* — Finnegan, Henderson, Farabow, Garrett & Dunner, L.L.P.

(57) ABSTRACT

A major object of the present invention is to provide a creamy O/W emulsion composition containing an adenosine phosphate ester, more specifically, to provide a creamy O/W emulsion composition containing an adenosine phosphate ester, which ensures emulsification stability and a superior feel during use. Specifically, the present invention provides a creamy O/W emulsion composition containing the following Components (A) to (F) at the following proportions based on its total amount:

(A) not less than 0.1 wt. % of adenosine phosphate ester selected from at least one member selected from the group consisting of cyclic adenosine 3',5'-monophosphate, adenosine monophosphate, adenosine diphosphate, adenosine triphosphate, and salts thereof;
(B) 0.5 to 6 wt. % of polyglycerin fatty acid ester;
(C) 0.05 to 0.7 wt. % of acrylic acid-alkyl methacrylate copolymer;
(D) 0.5 to 10 wt. % of amphiphilic lipid;
(E) 0.5 to 20 wt. % of polyhydric alcohol; and
(F) 0.3 to 5 wt. % of self-emulsifiable glycerin fatty acid ester.

9 Claims, No Drawings

CREAMY O/W EMULSION COMPOSITION AND PRODUCTION PROCESS THEREOF

TECHNICAL FIELD

The present invention relates to a creamy O/W emulsion composition containing an adenosine phosphate ester, which ensures emulsification stability and a superior feel during use; and a production process thereof.

BACKGROUND ART

Adenosine phosphate ester is known to have various physiological functions. To produce a preparation composition that can effectively exhibit the functions of the adenosine phosphate ester, it is necessary to incorporate a certain amount of adenosine phosphate ester in the composition. However, the adenosine phosphate ester is electrolytic, and therefore has a particular electrolyte characteristic, which decreases the strength of the oil/water interface layer in the emulsion composition. Therefore, a common defect in the production of an O/W emulsion composition containing an adenosine phosphate ester is the tendency of coalescence of the emulsified particles, which causes the separation of the water phase from the oil phase, and the emergence of oil or the like from the resulting emulsion. Moreover, even when there is no apparent change, the incorporation of adenosine phosphate ester can be a cause of deterioration of the emulsion system with time, and may rapidly decrease the viscosity of the emulsion.

In view of such problems, there were some attempts to obtain sufficient emulsification stability during the long-term storage of an O/W emulsion composition, for example, by adding a polyglycerin fatty acid ester, acrylic acid-alkyl methacrylate copolymer, alkanoyl lactic acid or its salt during the preparation of the O/W emulsion composition containing adenosine phosphate ester (refer to Patent Literature 1 (PTL 1)). In this composition, dispersion stability is maintained by utilizing electric repulsion of an ionic emulsifier, such as an alkanoyl lactic acid.

In general, a composition containing an ionic emulsifier is stable when the composition has a highly-fluidable liquid form, such as a skin milk; however, when it is a composition having a high viscosity, such as a creamy O/W emulsion composition, the stability of the system cannot be ensured without some kind of additive. Therefore, a method was attempted in which an O/W emulsion system was produced by containing a solid amphiphilic lipid such as a higher fatty acid, a higher alcohol or the like, in addition to the ionic emulsifier. However, when the system contains electrolytes in addition to the above combination of components, the system becomes unstable due to the electrolytes, and the stability of the composition decreases; consequently, it was not possible to maintain the viscosity for a long period. Particularly in the electrolyte-containing composition, separation or other defects of the composition is promoted by changes in temperature. For this reason, it has been difficult to obtain a stable electrolyte-containing composition while ensuring a high viscosity.

CITATION LIST

Patent Literature

PTL 1: Japanese Unexamined Patent Publication No. 2002-234830

SUMMARY OF INVENTION

Technical Problem

A major object of the present invention is to provide a creamy O/W emulsion composition containing an adenosine phosphate ester, which ensures superior emulsification stability even under high temperature or under preservation conditions with severe temperature changes.

Solution to the Problem

As a result of intensive study to solve the foregoing problems, the inventors of the present invention found that the addition of a self-emulsifiable glycerin fatty acid ester to an emulsion composition, which contains an adenosine phosphate ester, a polyglycerin fatty acid ester, an acrylic acid-alkyl methacrylate copolymer, an amphiphilic lipid, and a polyhydric alcohol significantly increases the emulsification property of the composition, and thereby makes it possible to produce an electrolyte-containing composition having high viscosity and emulsification stability. The present inventor further confirmed that such an emulsion composition has a high quality appearance, reduced stickiness during use, and a lubricating feel on the skin, and gives a superior feeling of comfort after use. The inventors conducted further studies based on these findings and completed the present invention.

As detailed below, the present invention provides a creamy O/W emulsion composition and a production process thereof; and an emulsion stabilization method of a creamy O/W emulsion composition containing an adenosine phosphate ester.

Item 1. A creamy O/W emulsion composition containing the following Components (A) to (F) at the following proportions based on its total amount, wherein the viscosity of the emulsion composition at 20° C. is 5000 to 60000 cps:

(A) not less than 0.1 wt. % of adenosine phosphate ester selected from at least one member selected from the group consisting of cyclic adenosine 3',5'-monophosphate, adenosine monophosphate, adenosine diphosphate, adenosine triphosphate, and salts thereof;
(B) 0.5 to 6 wt. % of polyglycerin fatty acid ester;
(C) 0.05 to 0.7 wt. % of acrylic acid-alkyl methacrylate copolymer;
(D) 0.5 to 10 wt. % of amphiphilic lipid;
(E) 0.5 to 20 wt. % of polyhydric alcohol; and
(F) 0.3 to 5 wt. % of self-emulsifiable glycerin fatty acid ester.

Item 2. The creamy O/W emulsion composition according to Item 1, wherein Component (B) is an ester of a $C_{12-36}$ fatty acid and a polyglycerin having a polymerization degree of 6 or more.

Item 3. The creamy O/W emulsion composition according to Item 1 or 2, wherein Component (C) has a $C_{5-40}$ alkyl group.

Item 4. The creamy O/W emulsion composition according to any one of Items 1 to 3, wherein Component (D) comprises at least one member selected from the group consisting of higher fatty acids, higher alcohols, mono alkyl glyceryl ethers, ceramides, ceramide saccharides, sugar lipids, lecithins, lecithin derivatives and structurally related compounds thereof.

Item 5. The creamy O/W emulsion composition according to any one of Items 1 to 4, wherein Component (E) is a trihydric alcohol.

Item 6. The creamy O/W emulsion composition according to any one of Claims 1 to 5, wherein Component (F) is a self-emulsifiable glycerin fatty acid ester which contains a hydrophilic surfactant to have a higher hydrophilicity.

Item 7. The creamy O/W emulsion composition according to any one of Items 1 to 6, further comprising (G) water in a proportion of 30 to 80 wt. %.

Item 8. The creamy O/W emulsion composition according to any one of Items 1 to 7, further comprising (H) oil in a proportion of 1 to 40 wt. %.

Item 9. The creamy O/W emulsion composition according to any one of Items 1 to 8, wherein the creamy O/W emulsion composition is a skin cosmetic, an externally-applied medicinal product for the skin, or a quasi drug for the skin.

Item 10. Use of the creamy O/W emulsion composition according to any one of Items 1 to 8 for production of a skin cosmetic, an externally-applied medicinal product for the skin, or an externally-applied quasi drug for the skin.

Item 11. A method for producing a creamy O/W emulsion composition containing the following Components (A) to (F) at the following proportions based on its total amount, wherein the viscosity of the emulsion composition at 20° C. is 5000 to 60000 cps:

(A) not less than 0.1 wt. % of adenosine phosphate ester;
(B) 0.5 to 6 wt. % of polyglycerin fatty acid ester;
(C) 0.05 to 0.7 wt. % of acrylic acid-alkyl methacrylate copolymer;
(D) 0.5 to 10 wt. % of amphiphilic lipid;
(E) 0.5 to 20 wt. % of polyhydric alcohol; and
(F) 0.3 to 5 wt. % of self-emulsifiable glycerin fatty acid ester, the method comprising the steps of:
1) preparing a non-aqueous emulsion using a composition containing (B) polyglycerin fatty acid ester, (D) amphiphilic lipid, (E) polyhydric alcohol and (F) self-emulsifiable glycerin fatty acid ester;
2) preparing an aqueous solution containing (A) at least one adenosine phosphate ester selected from the group consisting of cyclic adenosine 3'5'-monophosphate, adenosine monophosphate, adenosine diphosphate, adenosine triphosphate, and salts thereof, and (C) acrylic acid-alkyl methacrylate copolymer; and
3) mixing the non-aqueous emulsion and the aqueous solution under heat to produce an emulsion.

Item 12. An emulsion stabilization method for an adenosine-phosphate-ester-containing creamy O/W emulsion composition containing the following Components (A) to (F) at the following proportions based on its total amount, wherein the viscosity of the emulsion composition at 20° C. is 5000 to 60000 cps:

(A) not less than 0.1 wt. % of adenosine phosphate ester;
(B) 0.5 to 6 wt. % of polyglycerin fatty acid ester;
(C) 0.05 to 0.7 wt. % of acrylic acid-alkyl methacrylate copolymer;
(D) 0.5 to 10 wt. % of amphiphilic lipid;
(E) 0.5 to 20 wt. % of polyhydric alcohol; and
(F) 0.3 to 5 wt. % of self-emulsifiable glycerin fatty acid ester, the method comprising the steps of:
1) preparing a non-aqueous emulsion using a composition containing (B) polyglycerin fatty acid ester, (D) amphiphilic lipid, (E) polyhydric alcohol and (F) self-emulsifiable glycerin fatty acid ester;
2) preparing an aqueous solution containing (A) at least one adenosine phosphate ester selected from the group consisting of cyclic adenosine 3'5'-monophosphate, adenosine monophosphate, adenosine diphosphate, adenosine triphosphate, and salts thereof, and (C) acrylic acid-alkyl methacrylate copolymer; and
3) mixing the non-aqueous emulsion and the aqueous solution under heat to produce an emulsion.

Advantageous Effects of Invention

The present invention suppresses separation, oil emergence, gelation and the like of a creamy O/W emulsion composition containing an adenosine phosphate ester, which is generally difficult to be emulsified. The O/W emulsion composition of the present invention thereby ensures superior emulsification stability even under high temperature or under preservation condition with severe temperature changes.

The creamy O/W emulsion composition of the present invention is capable of stable incorporation of a large amount of adenosine phosphate ester, and therefore is useful as a cosmetic, an externally-applied skin product (medicinal product or quasi drug) or the like that uses an adenosine phosphate ester as the active ingredient. Especially, the present invention allows O/W emulsion compositions containing adenosine monophosphate (AMP) or a salt thereof to efficiently exhibit moistening effects or skin turnover promotion effects that are derived from the substance, and improves usability as a cosmetic or an external skin preparation for anti-aging of skin or skin condition improvement, such as the prevention of wrinkles, improvement in skin resilience.

Moreover, in addition to emulsification stability during prolonged storage, the emulsion composition of the present invention is provided with a high quality appearance and has a texture that is much less greasy or sticky, because of the appropriate selection or adjustment of the ratio of the components such as adenosine phosphate ester, polyglycerine fatty acid ester, amphiphilic lipid, acrylic acid-alkyl methacrylate copolymer, polyhydric alcohol, self-emulsifiable glycerin fatty acid ester, etc. The present invention thus provides a smooth creamy O/W emulsion composition ensuring greater availability of the use.

Therefore, the creamy O/W emulsion composition of the present invention is particularly useful as a medicinal product, particularly as an external preparation, such as a skin cosmetic (incl. scalp cosmetics), an externally-applied skin (incl. scalp) medicinal product or quasi drug.

The present invention also provides a method for improving emulsification stability of a creamy O/W emulsion composition containing a relatively large amount of adenosine phosphate ester. Accordingly, the method of the present invention allows for easy production of a creamy O/W emulsion composition containing adenosine phosphate ester, while enabling efficient expression of the various physiological functions of adenosine phosphate ester.

DESCRIPTION OF EMBODIMENTS

1. Creamy O/W Emulsion Composition

The creamy O/W emulsion composition of the present invention is characterized by comprising the following Components (A) to (F). The following specifically describes the component of the present invention.

Component (A): Adenosine Phosphate Ester

The adenosine phosphate ester used for the present invention is not particularly limited. Preferable examples include various adenosine phosphate esters that can exhibit physiological functions when applied to the skin, incorporated in various external preparations, particularly cosmetics, externally-applied medicinal products, or quasi drugs. The adenosine phosphate ester is preferably water-soluble or hydrophilic.

Examples of adenosine phosphate esters include cyclic adenosine 3',5'-monophosphate, adenosine monophosphate (AMP), adenosine diphosphate, adenosine triphosphate, and salts thereof, preferably cyclic adenosine 3',5'-monophosphate, adenosine monophosphate, adenosine diphosphate and salts thereof. They can be used singly or in combination of two or more.

Examples of such salts include sodium salts, potassium salts, and like alkali metal salts; calcium, magnesium, barium, and like alkaline earth metal salts; arginine, lysine and like basic amino acid salts; ammonium, tri-cyclohexyl ammonium, and like ammonium salts; mono isopropanolamine, diisopropanol mine, triisopropanol amine and like alkanolamine salts. Among them, alkali metal salts are particularly preferable.

Preferable examples of Component (A) used for the present invention include adenosine monophosphate monosodium, adenosine monophosphate disodium, adenosine triphosphate monosodium, adenosine triphosphate disodium, adenosine triphosphate trisodium, and cyclic adenosine 3',5'-monophosphate.

Adenosine phosphate esters are phosphorylated in the cell and converted into ATP, which serves as an energy source. When applied to a skin area having a problem such as aging, a composition containing adenosine phosphate esters is percutaneously absorbed, and promotes ATP generation in the cell. The increase in the intracellular ATP level activates the metabolism of skin cells, promotes the cell cycle, and thereby accelerates skin turnover. The skin turnover acceleration encourages the discharge of old horny cell layers and the provision of new horny cell layers. This facilitates water retention of the skin and makes the skin softer and more resilient, making the skin smoother and reducing dullness.

The proportion of the adenosine phosphate ester in the emulsion composition of the present invention is not particularly limited insofar as the desired effect of the adenosine phosphate ester is ensured. Although it depends on the type of the adenosine phosphate ester, the proportion is generally at least 0.1 wt. %, preferably 0.5 to 7 wt. %, more preferably 1 to 6 wt. %, based on the total weight (100 wt %) of the final emulsion composition.

Component (B): Polyglycerin Fatty Acid Ester

Polyglyceryin fatty acid esters usable in the present invention are not limited. Examples include esters of a $C_{12-36}$ fatty acid and polyglycerins having a degree of polymerization of 6 or more, especially 6 to 10. Fatty acids that form esters with polyglycerins include saturated, unsaturated, linear, and branched fatty acids. Specific examples are capric acid, lauric acid, isotridecanoic acid, myristic acid, palmitic acid, palmitoleic acid, stearic acid, isostearic acid, oleic acid, linoleic acid, behenic acid, and ricinolic acid.

Specific examples of polyglycerin fatty acid esters are hexaglyceryl monolaurate, hexaglyceryl monoisostearate, hexaglyceryl monomyristate, hexaglyceryl dioleate, hexaglyceryl dimyristate, hexaglyceryl dipalmitate, hexaglyceryl distearate, hexaglyceryl dibehenylate, hexaglyceryl trilaurate, hexaglyceryl trimyristate, hexaglyceryl tripalmitate, hexaglyceryl tristearate, hexaglyceryl tribehenylate, hexaglyceryl tetralaurate, hexaglyceryl tetramyristate, hexaglyceryl tetrapalmitate, hexaglyceryl tetrastearate, hexaglyceryl tetrabehenylate, hexaglyceryl pentalaurate, hexaglyceryl pentamyristate, hexaglyceryl pentapalmitate, hexaglyceryl pentastearate, hexaglyceryl pentabehenylate, decaglyceryl monocaprate, decaglyceryl monolaurate, decaglyceryl monomyristate, decaglyceryl monopalmitate, decaglyceryl monostearate, decaglyceryl monooleate, decaglyceryl monolinoleate, decaglyceryl monoisostearate, decaglyceryl dicaprate, decaglyceryl dilaurate, decaglyceryl dimyristate, decaglyceryl dipalmitate, decaglyceryl distearate, decaglyceryl diisostearate, decaglyceryl trilaurate, decaglyceryl trimyristate, decaglyceryl tripalmitate, decaglyceryl tristearate, decaglyceryl trioleate, decaglyceryl tribehenylate, decaglyceryl pentastearate, decaglyceryl pentaoleate, decaglyceryl pentaisostearate, decaglyceryl heptastearate, decaglyceryl decastearate, decaglyceryl decaoleate, and decaglyceryl decaisostearate. However, the polyglycerin fatty acid esters are not limited thereto.

Such polyglycerin fatty acid esters may be used singly or in a combination of two or more. Polyglycerin fatty acid esters having an HLB value of 10 or more, especially 10 to 15, can be suitably used. It is preferable to use the polyglycerin fatty acid ester in a proportion of 0.5 to 6 wt. %, and more preferably 1 to 5.5 wt. %, based on the total weight (100 wt. %) of the composition.

Component (C): Acrylic Acid-Alkyl Methacrylate Copolymer

Acrylic acid-alkyl methacrylate copolymers usable in the invention are not particularly limited. Typical examples include those having an alkyl chain with 5 to 40 carbons. Preferred are those having an alkyl chain with 10 to 30 carbons. For the sake of convenience, commercially available products can be used. Specific examples of such products include, but are not limited to, Carbopol 1342, Carbopol ETD2020, Pemulen TR-1, Pemulen TR-2 (all of the above are trade names and available from Lubrizol Corporation).

Such acrylic acid-alkyl methacrylate copolymers may be used singly or in combination of two or more. It is preferable to use the acrylic acid-alkyl methacrylate copolymer in a proportion of 0.05 to 0.7 wt. %, more preferably in a proportion of 0.1 to 0.6 wt. %, based on the total weight (100 wt. %) of the final emulsion composition.

Component (D): Amphiphilic Lipid

"Amphiphilic lipid" is the general name for a solid lipid which has both a "hydrophilic group" (hydrophilic functional group) and a "lipophilic group" (hydrophobic functional group) in a molecule. The amphiphilic lipid is not soluble in water, and tends to be dispersed in water.

Component (D) is not limited as long as it is pharmacologically or cosmetically acceptable. Examples include higher fatty acids, higher alcohols, mono alkyl glyceryl ethers, sphingolipid, glycolipid, lecithin, lecithin derivatives and structurally related compounds thereof. More specifically, higher fatty acids ($C_{14-22}$) such as myristic acids, stearic acids, oleic acids, palmitic acids, and behenic acids; higher alcohols such as linear or branched saturated or unsaturated alcohols ($C_{8-22}$) including octanol, myristyl alcohol, cetyl alcohol, cetostearyl alcohol, stearyl alcohol, behenyl alcohol, isostearyl alcohol, cholesterol, and phytosterol; monoalkyl glycerylether (alkyl carbon number=8 to 22) such as chimyl alcohol, batyl alcohol (glyceryl monostearyl ether), selachyl alcohol, isostearyl glycerylether, or mono docosa glyceryl ether; sphingolipids such as ceramide, phytosphingosine, and glycosides thereof (ceramide saccharides, etc.); glycolipids such as galactolipid, sulfolipid, and sphingoglycolipid; lecithins such as soybean lecithin, egg-yolk lecithin, and lysolecithin; lecithin derivatives ("derivative" here denotes a lecithin or the like hydrogenated or hydroxylated with an unsaturated bond of an alkyl group) such as hydrogenated soybean phospholipids, partially-hydrogenated soybean phospholipids, hydrogenated egg-yolk phospholipids, partially-hydrogenated egg-yolk phospholipids, soybean phospholipid hydroxide, and hydrogenated soybean lysophospholipids; and phospholipid fractions in lecithins such as phosphatidylcholine, phosphatidyl ethanol amine, phosphatidyl inositol, and sphingomyelin.

Among them, amphiphilic lipids selected from higher fatty acids, higher alcohols, mono alkyl glyceryl ethers, lecithins, and lecithin derivatives are preferably used as Component (D). By using such amphiphilic lipids, it is possible to obtain an O/W emulsion composition which ensures superior emulsification stability and thereby significantly suppresses gelation, the emergence of oil or like problems even under high temperatures or storage conditions with severe temperature changes.

The amphiphilic lipids can be used singly or in a combination of two or more. Though it depends on the dosage form or some other factors, the proportion of the amphiphilic lipids is generally 0.5 to 10 wt. %, more preferably 0.5 to 5 wt. %, further preferably 0.5 to 3 wt. %, based on the total weight (100 wt. %) of the final emulsion composition. Among various combinations, the combination of soybean lecithin and batyl alcohol exhibits particularly superior emulsification stability.

Component (E): Polyhydric Alcohol

The emulsion composition of the present invention contains a polyhydric alcohol which further improves the expression of the emulsification property of the polyglycerin fatty acid ester etc.

Polyhydric alcohols usable herein are not particularly limited. Specific examples include dihydric alcohols such as ethylene glycol, diethylene glycol, polyethylene glycol, 1,3-butylene glycol, propylene glycol, dipropylene glycol, isoprene glycol, and pentadiol; trihydric alcohol such as glycerin (incl. concentrated glycerin); polyglycerins having a polymerization degree of 2 to 10 (e.g., diglycerin, triglycerin, tetraglycerin; sugar alcohols such as sorbitol, maltitol, and fructose. Among them, glycerin is particularly preferable. Such polyhydric alcohols may be used singly or in combination. The proportion of the polyhydric alcohol is 0.5 to 20 wt. %, preferably 1 to 15 wt. %, based on the total weight of the final emulsion composition.

Component (F): Self-Emulsifiable Glycerin Fatty Acid Ester

The emulsion composition of the present invention contains a self-emulsifiable glycerin fatty acid ester, which imparts electrolyte resistance to an O/W emulsion, and stabilizes the emulsion system. The self-emulsifiable glycerin fatty acid ester is a lipophilic emulsifier having a nonionic surface-activation effect, which is obtained by mixing a hydrophilic surfactant such as a fatty acid soap or polyethylene glycol fatty acid ester with a glycerin fatty acid ester so that the glycerin fatty acid ester is dispersed in water. In the self-emulsifiable glycerin fatty acid ester used herein, the glycerin fatty acid ester is preferably formed of mono glycerin, such as self-emulsifiable glyceryl monomyristate, self-emulsifiable glyceryl monostearate, and self-emulsifiable glyceryl monooleate, more preferably, self-emulsifiable glyceryl monostearate.

A commercially available self-emulsifiable glycerin fatty acid ester can be used as the Component (F) in the present invention. For example, Leodol MS165V (Kao Corporation); NIKKO L MGS-150V (Nikko Chemicals), NIKKOL MGS-ASEV (Nikko Chemicals) can be used.

Such self-emulsifiable glycerin fatty acid esters can be used singly or in a combination of two or more. It is preferable to use the self-emulsifiable glycerin fatty acid ester in a proportion of 0.3 to 5 wt. %, more preferably in a proportion of 0.5 to 4 wt. %, based on the total weight (100 wt. %) of the final emulsion composition.

In addition to Components (A) to (F) above, the O/W emulsion composition of the present invention contains the following Component (G): water, and Component (H): oil at predetermined proportions.

Component (G): Water

The O/W emulsion composition of the present invention contains water, such as distilled water, ion exchanged water, sterile water, purified water, or water containing adenosine phosphate ester. Examples of the water containing adenosine phosphate ester include sea water, hot spring water, and mineral water. The sea water may be any of surface water, intermediate water, deep sea water or super deep water.

The proportion of the water is not particularly limited; however, the proportion is typically in the range of 30 to 80 wt. %, more preferably 40 to 70 wt. %, based on the total weight (100 wt. %) of the final emulsion composition.

Component (H): Oil

Oils usable in the invention are not particularly limited. Specific examples include peanut oil, sesame oil, soybean oil, safflower oil, avocado oil, sunflower oil, corn oil, rapeseed oil, cottonseed oil, castor oil, camellia oil, coconut oil, olive oil, poppy oil, cacao oil, jojoba oil, and like vegetable oils; beef tallow, lard, lanolin, and like animal oils and fats; petrolatum, liquid paraffin, squalane, botanical squalane, α-olefin oligomers, and like hydrocarbon liquid oils; isopropyl myristate, isopropyl isostearate, myristyl myristate, cetyl palmitate, cetyl isooctate, isocetyl myristate, n-butyl myristate, octyldodecyl myristate, isopropyl linolenate, propyl ricinoleate, isopropyl ricinoleate, isobutyl ricinoleate, heptyl ricinoleate, diethyl sebacate, diisopropyl adipate, and like higher fatty acid esters; white beeswax, whale wax, Japan wax, and like waxes; microcrystalline wax, paraffin wax, and like waxes; glyceryl oils such as aceto glyceryl, glyceryl triisooctate, glyceryl triisostearate, glyceryl triisopalmitate, glyceryl tri-2-ethylhexanoate, glyceryl monostearate, glyceryl dibehenate, glyceryl tri myristate, tri(caprylic/capric acid) glyceryl, mono-, di-, or triglyceride mixtures of $C_{12-18}$ saturated or unsaturated fatty acids; methyl polysiloxane, dimethyl polysiloxane, methylphenyl polysiloxane, methyl hydrogen polysiloxane, and like linear silicones; decamethylcyclopentasiloxane, octamethylcyclotetrasiloxane, methylcyclosiloxane, and like cyclic silicones; crosslinked methyl polysiloxane, crosslinked methylphenyl polysiloxane, and like crosslinked silicones; and, for example, silicone oils such as modified silicones which are modified by polyoxyethylene or polyoxypropylene, and the like.

Such oils may be used singly or in combination. It is preferable to use the oil in a proportion of 1 to 40 wt. %, more preferably in a proportion of 5 to 30 wt. %, further preferably in a proportion of 10 to 30 wt. %, based on the total weight % (100 wt. %) of the final emulsion composition.

The emulsion composition of the present invention is prepared by appropriately combining the above compounds, i.e., Components (A) to (H). The following are some preferable combinations.

Combination (i)

Component (A) adenosine monophosphate disodium; Component (B) decaglyceryl monostearate; Component (C) acrylic acid-alkyl methacrylate copolymer; Component (D) cetyl alcohol, hydrogenated soybean phospholipid, stearic acid, behenyl alcohol; Component (E) concentrated glycerin, dipropylene glycol; Component (F) self-emulsifiable glyceryl monostearate; Component (G) purified water; and Component (H) tri(caprylic/capric acid) glyceryl, methyl polysiloxane.

Combination (ii)

Component (A) adenosine monophosphate disodium; Component (B) decaglyceryl monomyristate; Component (C) acrylic acid-alkyl methacrylate copolymer; Component (D) stearic acid, behenyl alcohol; Component (E) concentrated glycerin, dipropylene glycol; Component (F) self-emulsifiable glyceryl monooleate; Component (G) purified water; and Component (H) liquid paraffin, tri(caprylic/capric acid) glyceryl, methyl polysiloxane.

Combination (iii)

Component (A) adenosine monophosphate monosodium; Component (B) decaglyceryl monomyristate, decaglyceryl monostearate; Component (C) acrylic acid-alkyl methacrylate copolymer; Component (D) stearic acid, behenyl alcohol; Component (E) concentrated glycerin; Component (F) self-emulsifiable glyceryl monostearate; Component (G) purified water; and Component (H) liquid paraffin, tri(caprylic/capric acid) glyceryl, methyl polysiloxane.

Combination (iv)

Component (A) adenosine triphosphate monosodium; Component (B) decaglyceryl monomyristate; Component (C) acrylic acid-alkyl methacrylate copolymer; Component (D) batyl alcohol, hydrogenated soybean phospholipid, stearic acid, behenyl alcohol; Component (E) concentrated glycerin; Component (F) self-emulsifiable glyceryl monostearate; Component (G) purified water; and Component (H) liquid paraffin, tri(caprylic/capric acid) glyceryl, methyl polysiloxane.

Combination (v)

Component (A) adenosine triphosphate disodium; Component (B) decaglyceryl monostearate; Component (C) acrylic acid-alkyl methacrylate copolymer; Component (D) cholesterol, stearic acid, behenyl alcohol; Component (E) concentrated glycerin, dipropylene glycol; Component (F) self-emulsifiable glyceryl monooleate; Component (G) purified water; and Component (H) liquid paraffin, tri(caprylic/capric acid) glyceryl, methyl polysiloxane.

Combination (vi)

Component (A) adenosine triphosphate trisodium; Component (B) decaglyceryl monomyristate; Component (C) acrylic acid-alkyl methacrylate copolymer; Component (D) stearic acid, behenyl alcohol; Component (E) concentrated glycerin; Component (F) self-emulsifiable glyceryl monostearate; Component (G) purified water; and Component (H) tri(caprylic/capric acid) glyceryl, methyl polysiloxane.

Combination (vii)

Component (A) cyclic adenosine 3',5'-monophosphate; Component (B) decaglyceryl monostearate; Component (C) acrylic acid-alkyl methacrylate copolymer; Component (D) batyl alcohol, stearic acid, behenyl alcohol; Component (E) concentrated glycerin; Component (F) self-emulsifiable glyceryl monomyristate; Component (G) purified water; and Component (H) liquid paraffin, tri(caprylic/capric acid) glyceryl, methyl polysiloxane.

Combination (viii)

Component (A) adenosine phosphate; Component (B) decaglyceryl monomyristate; Component (C) acrylic acid-alkyl methacrylate copolymer; Component (D) hydrogenated soybean phospholipid, cholesterol, stearic acid, behenyl alcohol; Component (E) concentrated glycerin, dipropylene glycol; Component (F) stearyl self-emulsifiable glyceryl monostearate; Component (G) purified water; and Component (H) liquid paraffin, tri(caprylic/capric acid) glyceryl, methyl polysiloxane.

(I) Other Components

The composition for external use of the present invention generally has a pH from mildly acidic to neutral; however, to reduce skin irritation and to ensure a pigmentation prevention effect, the pH preferably falls within pH 5 to 7, and more preferably pH 5.5 to 7. To adjust the pH of the composition for external use of the present invention within this range, a pH adjuster may be added to the composition for external use. The pH adjuster is not limited as long as it is mildly alkaline to alkaline and pharmacologically or cosmetically acceptable. Examples of the pH adjuster include sodium hydroxide, potassium hydroxide, L-arginine, amino methyl propane diol, diisopropanol amine, and triethanolamine.

Insofar as the effect of the present invention is not impaired, the creamy O/W emulsion composition of the present invention may contain various additives including surfactants, colorants (dyes, pigments), aromatic substances, antiseptics, bactericides, thickeners, antioxidants, sequestrants, deodorizers; and other known ingredients such as moisturizers, UV absorbers, UV scattering agents, vitamins, plant extracts, skin astringents, antiinflammatory agents, skin-whitening agents, anti-oxidants, and cell activators; particularly, various known ingredients for use in externally-applied compositions for the skin, such as cosmetics, externally-applied medicinal products or quasi drugs.

In the creamy O/W emulsion composition of the present invention, separation of the oil component is significantly suppressed during prolonged storage with varied temperatures, even when the emulsion composition contains the desired amount of adenosine phosphate ester to ensure the desired target usage and effect, for example, not less than 0.1 wt. %, preferably 0.1 to 6 wt. %. The creamy O/W emulsion composition of the present invention thus maintains a stable emulsion state. Further, depending on the target usage, the creamy O/W emulsion composition of the present invention can be so formed that it has the least stickiness and provides a superior feel on skin during use. Therefore, the creamy O/W emulsion composition of the present invention is particularly useful as an external preparation, such as a cosmetic, externally-applied medicinal product or quasi drug, which are applied to the skin (incl. scalp). Particularly, when using adenosine monophosphate (AMP) or a salt thereof as an adenosine phosphate ester, the creamy O/W emulsion composition of the present invention can be formed as a cosmetic or an externally-applied skin preparation (medicinal product, quasi drug) having an improved effect of moisturizing, preventing dryness or aging, or easing skin problems, based on the effect of the AMP or the salt thereof.

The creamy O/W emulsion composition of the present invention can be formed as a creamy external preparation such as a cosmetic or a skin external preparation (medicinal product, quasi drug). The form of the creamy external preparation is not limited, and may be an emollient cream, massage cream, cleansing cream, makeup cream or the like. The external preparation is used by being applied to the skin of the consumer in an adequate dose per day or at an adequate frequency per day according to the age, sex, purpose, and the degrees of skin damage of the user.

2. Production Process

The creamy O/W emulsion composition of the present invention contains (A) at least 0.1 wt. % of adenosine phosphate ester; (B) 0.5 to 6 wt. % of polyglycerin fatty acid ester, (C) 0.05 to 0.7 wt. % of acrylic acid-alkyl methacrylate copolymer; (D) 0.5 to 10 wt. % of amphiphilic lipid; (E) 0.5 to 20 wt. % of polyhydric alcohol; and (F) 0.3 to 5 wt. % of self-emulsifiable glycerin fatty acid ester, based on its total amount. Although the method of preparation is not particularly limited, the following method is preferred.

1) First, a non-aqueous system composition is prepared by stirring under heat a mixture of Component (B): polyglycerin fatty acid ester, Component (D): amphiphilic lipid, Component (E): polyhydric alcohol, Component (F): self-emulsifiable glycerin fatty acid ester and Component (G): oil to evenly dissolve the components.

2) Next, a separately-prepared aqueous solution (aqueous system composition) containing Component (A): adenosine phosphate ester, Component (C): acrylic acid-methacrylic acid alkyl copolymer and Component (H): water is heated to mix the components, and the mixture is emulsified with the above non-aqueous emulsion at 60° C. to 80°

C. Thereafter, the obtained emulsion was cooled to prepare a creamy O/W emulsion composition.

Here, the proportion of Component (G): oil to Component (H): water is the same as Section 1 above.

In the emulsion step 2), after mixing the non-aqueous emulsion and the aqueous solution (aqueous system composition), the lower alcohol may be added when cooling the mixture. This further improves the percutaneous absorption of the adenosine phosphate ester.

The lower alcohol added after mixing the non-aqueous emulsion and the aqueous solution is not particularly limited, and can be appropriately selected from $C_{1-6}$ alcohols. Preferable examples of the lower alcohols include $C_{1-4}$ alcohols such as ethanol, propanol, and isopropanol. These lower alcohols may be used singly or in combination of two or more. Ethanol is particularly preferable. In this case, the proportion of the lower alcohol is 0.5 to 10 wt. %, preferably 1 to 7 wt. %, based on the total weight (100 wt. %) of the final emulsion composition.

The above-mentioned aqueous solution (aqueous system composition) may further contain a polyhydric alcohol to adjust the moistening performance and/or the sensory characteristic of the final emulsion composition to a desired extent. Here, the polyhydric alcohol may be arbitrarily selected from the above alcohols; however, when the non-aqueous system composition contains a polyhydric alcohol, it is preferable to use the same polyhydric alcohol as used in the non-aqueous system composition, or a polyhydric alcohol having a higher compatibility than the polyhydric alcohol used in the non-aqueous composition.

The method for emulsifying the non-aqueous system composition and the aqueous solution (aqueous system composition) may be performed by stirring under normal pressure or high pressure using a homomixer or the like. As required, the obtained emulsion may be made finer using a homogenizer.

The proportion of the non-aqueous system composition to the aqueous solution (aqueous system composition) is not particularly limited; however, the proportion of the non-aqueous emulsion is preferably 1 to 40 wt. %, more preferably 5 to 35 wt. %, based on the total weight of the final emulsion composition. The proportion range ensures the stability of the obtained creamy O/W emulsion composition.

The viscosity of the creamy O/W emulsion composition of the present invention is not particularly limited; however, when used for cosmetics, external medicinal products, or external quasi drugs applied to the skin, the viscosity is preferably not more than 60000 cps, preferably 5000 to 60000 cps, more preferably 10000 to 50000 cps, further preferably 15000 to 40000 cps, still further preferably 15000 to 33000 cps, particularly preferably 20000 to 30000 cps, based on the viscosity measured by a B-type viscometer rotor No. 4, at 6 rpm, 20° C.

The viscosity of the creamy O/W emulsion composition of the present invention can be controlled by appropriately adjusting the proportions of Components (A) to (F). For example, an increase in the proportion of Component (C) or Component (D) tends to increase the viscosity; in contrast, an increase in the proportion of Component (E) tends to decrease the viscosity. Therefore, by adjusting the proportions of Components (A) to (F) within the above ranges in consideration of such a tendency, it is possible to obtain a creamy O/W emulsion composition ensuring both stability as an O/W emulsion composition and a desired viscosity.

By setting the viscosity of the creamy O/W emulsion composition of the present invention within the above range, the emulsion composition becomes easy to apply, has a desirable spreadability, and ensures a superior feel during use.

3. Emulsion Stabilization Method for a Creamy O/W Emulsion Composition Containing Adenosine Phosphate Ester The present invention further provides an emulsion stabilization method for a creamy O/W emulsion composition containing an adenosine phosphate ester. This method is carried out by preparing a creamy O/W emulsion composition using an acrylic acid-alkyl methacrylate copolymer, a polyglycerin fatty acid ester, an amphiphilic lipid, a polyhydric alcohol and a self-emulsifiable glycerin fatty acid ester, water, oil, and the like, in addition to the adenosine phosphate ester.

More specifically, the O/W emulsion composition contains at least 0.1 wt. %, preferably 0.5 to 7 wt. %, more preferably 1 to 6 wt. % of adenosine phosphate ester; 0.5 to 6 wt. %, preferably 1 to 5.5 wt. % of polyglycerin fatty acid ester; 0.05 to 0.7 wt. %, preferably 0.1 to 0.6 wt. % of acrylic acid-alkyl methacrylate copolymer; 0.5 to 10 wt. %, more preferably 0.5 to 5 wt. %, further preferably 0.5 to 3 wt. % of amphiphilic lipid; 0.5 to 20 wt. %, more preferably 1 to 15 wt. % of polyhydric alcohol; and 0.3 to 5 wt. %, preferably 0.5 to 4 wt. % of self-emulsifiable glycerin fatty acid ester, based on the total amount of the final O/W emulsion composition of (100 wt. %). In this case, the proportion of oil in the final creamy O/W emulsion composition is not limited, but preferably 1 to 40 wt. %, more preferably 5 to 35 wt. %, further preferably 10 to 30 wt. %. The remainder of the composition, which does not include the oil and afore-mentioned various components, is water. Although it is not particularly limited, the water content is adjusted within a range from 30 to 80 wt. %, preferably 40 to 70 wt. %.

Specifically, the emulsion stabilization method of the present invention can be carried out by preparing the creamy O/W emulsion composition with the afore-mentioned proportions of the components in the following manner.
1) First, a non-aqueous system composition is prepared by stirring under heat a mixture of a polyglycerin fatty acid ester, an amphiphilic lipid, oil, a polyhydric alcohol, and a self-emulsifiable glycerin fatty acid ester to evenly dissolve the components.
2) Next, a separately-prepared aqueous solution (aqueous system composition) containing an adenosine phosphate ester, water and an acrylic acid-methacrylic acid alkyl copolymer is heated to mix the components, and the mixture is emulsified with the above non-aqueous system emulsion at 60° C. to 80° C. Thereafter, the obtained emulsion was cooled to prepare a creamy O/W emulsion composition.

By preparing a creamy O/W emulsion composition in such a manner, it is possible to impart emulsion stability to a formulation having a relatively high viscosity. Accordingly, the above method produces an emulsion composition in which separation is significantly inhibited and stable emulsion conditions are maintained during long periods of storage under high temperatures or varied temperatures.

EXAMPLE

The following describes the examples of the present invention. However, the present invention is not limited to these examples.

Examples 1 to 8

A polyglycerin fatty acid ester, an amphiphilic lipid, oil, a polyhydric alcohol, and a self-emulsifiable glycerin fatty acid ester were mixed and dissolved by heating to obtain a uniform non-aqueous system composition. An aqueous system composition (aqueous solution), which was separately prepared by dissolving an adenosine phosphate ester (adenosine monophosphate disodium, cyclic adenosine 3',5'-monophosphate or adenosine triphosphate sodium), an acrylic acid-alkyl methacrylate copolymer, a pH adjuster and the like in purified water, was added to the non-aqueous system composition under heat, and the mixture was stirred at 80° C. by a homomixer. Thereafter, the obtained mixture was cooled to be completed as an emulsion composition of the present invention (Examples 1 to 8). Table 1 shows the proportions of the components in the final composition.

Each of the eight types of emulsion compositions (Examples 1 to 8) thus prepared was taken to three transparent glass vials. After storage under the following conditions (i) to (iii), the appearance (separation, oil emergence, rapid decrease in viscosity) of the emulsion composition were visually examined, and evaluated according to the following criteria.

The conditions (i) to (iii) are:
(i) storage for one month under 40° C.
(ii) storage for two weeks under 60° C.
(iii) 15 rounds of a 24-hour cycle test were performed at −5° C. to 40° C.

Criteria
Good: none of separation, oil emergence, and rapid decrease in viscosity was seen.
Poor: either of separation, oil emergence, or rapid decrease in viscosity was seen.

The "separation" is a phenomenon in which the oil phase and the water phase are separated due to degradation of the emulsion system. "Oil emergence" is also called "creaming" in which the components of the oil phase come up to the liquid surface as oil droplets due to the decrease in the interfacial film strength between oil and water phases.

In addition to the evaluation of the appearance, the viscosity immediately after the formulation was measured using a B-type viscometer (BL-type; Tokyo Keiki Inc.) rotor No. 4 at 6 rpm, 20° C. The following table shows the measurement results.

For comparison, using the same method as those for Examples 1 to 8, an emulsion composition (Comparative Example 1) which does not contain a polyhydric alcohol, and an emulsion composition (Comparative Example 2) containing an lipophilic glycerin fatty acid ester instead of the self-emulsifiable mono glycerin fatty acid ester were prepared, as shown in Table 2. They were subjected to a storage stability test in the same manner as above.

Tables 1 and 2 show the results of the stability conservation tests for the respective emulsion compositions of Examples 1 to 8 and Comparative Examples 1 and 2.

Leodol MS165V (Kao Corporation) was used as the self-emulsifiable glyceryl monostearate, Pemulen TR-2 (Lubrizol Corporation) was used as the acrylic acid-alkyl methacrylate copolymer, and polyglyceryl monomyristate (Nikko Chemicals) was used as the lipophilic glyceryl monostearate.

TABLE 1

The values are proportions (weight %) based on the total weight of the final composition (100 weight %).

| | | Example 1 | Example 2 | Example 3 | Example 4 | Example 5 | Example 6 | Example 7 | Example 8 |
|---|---|---|---|---|---|---|---|---|---|
| 1 | Adenosine monophosphate disodium | 0.5 | 1 | 1.5 | 3 | | | | |
| 2 | Cyclic adenosine 3',5'-monophosphate | | | | | 0.1 | 0.5 | | |
| 3 | Adenosine triphosphate disodium | | | | | | | 0.3 | 1 |
| 4 | Decaglyceryl monomyristate | | 1.5 | 2 | 2 | | 1.5 | | 1.6 |
| 5 | Decaglyceryl monostearate | 2 | | 0.5 | | 1.4 | | 1.2 | |
| 6 | Self-emulsifiable glyceryl monomyristate | 1 | 0.9 | 0.8 | 0.8 | 1.5 | 1 | 0.9 | 0.7 |
| 7 | Batyl alcohol | 1 | 1 | | 1 | | | | |
| 8 | Stearate | 1 | | 0.8 | 1 | | 0.8 | 0.8 | 0.8 |
| 9 | Behenyl alcohol | | 1.5 | 2 | 2 | 0.9 | 1.5 | | 2 |
| 10 | Liquid paraffin | | 8 | 10 | 6 | 4 | | 5 | 8 |
| 11 | Tri(caprylic/capric acid)glyceryl | 8 | 4 | 2 | 6 | 4 | 10 | 8 | 9 |
| 12 | Methyl polysiloxane | 0.5 | 1 | 1 | 0.5 | 0.5 | 0.5 | 1 | 1 |
| 13 | Concentrated glycerin | 1 | 3 | 5 | 5 | 2 | 5 | 3 | 5 |
| 14 | Dipropylene glycol | 4 | 2 | | | 2 | | | 3 |
| 15 | Acrylic acid-alkyl methacrylate copolymer | 0.05 | 0.15 | 0.15 | 0.2 | 0.1 | 0.1 | 0.15 | 0.15 |
| 16 | pH adjuster | q.s*. | q.s. | q.s. | q.s. | q.s. | q.s. | q.s. | q.s. |
| 17 | Antiseptic | q.s. | q.s. | q.s. | q.s. | q.s. | q.s. | q.s. | q.s. |
| 18 | Purified water | R** | R | R | R | R | R | R | R |
| | Viscosity (B-type viscometer rotor No. 4, 6 rpm, 20° C.) | 15000 | 33000 | 25000 | 27000 | 20000 | 28000 | 32000 | 25000 |
| | Stability with time 40° C., 1 month | Good | Good | Good | Good | Good | Good | Good | Good |
| | Stability with time 60° C., 2 weeks | Good | Good | Good | Good | Good | Good | Good | Good |

TABLE 1-continued

The values are proportions (weight %) based on the total weight of the final composition (100 weight %).

| | Example 1 | Example 2 | Example 3 | Example 4 | Example 5 | Example 6 | Example 7 | Example 8 |
|---|---|---|---|---|---|---|---|---|
| Stability with time cycle (−5 to 40° C.) 2 weeks | Good | Good | Good | Good | Good | Good | Good | Good |

Notes:
*q.s. = quantum sufficiat
**R = remainder

TABLE 2

| | | Comparative Example 1 | Comparative Example 2 |
|---|---|---|---|
| 1 | Adenosine monophosphate disodium | 3.0 | 3.0 |
| 2 | Decaglyceryl monomyristate | 2.0 | 2.0 |
| 3 | Decaglyceryl monostearate | | |
| 4 | Self-emulsifiable glyceryl monomyristate | 0.8 | |
| 5 | Lipophilic glyceryl monostearate | | 1.0 |
| 6 | Batyl alcohol | 0.9 | 0.5 |
| 7 | Hydrogenated soybean phospholipid | | 0.1 |
| 8 | Stearate | 1.0 | |
| 9 | Behenyl alcohol | 2.0 | 2.0 |
| 10 | Liquid paraffin | 6.0 | 8.0 |
| 11 | Tri(caprylic/capric acid)glyceryl | 6.0 | 5.0 |
| 12 | Methyl polysiloxane | 0.5 | 0.3 |
| 13 | Purified glycerin | | 6.0 |
| 14 | Dipropylene glycol | | |
| 15 | Acrylic acid-alkyl methacrylate copolymer | 0.2 | 0.2 |
| 16 | pH adjuster | q.s. | q.s. |
| 17 | Antiseptic | q.s. | q.s. |
| 18 | Purified water | remainder | remainder |
| | Stability with time 40° C., 1 month | Poor | Good |
| | Stability with time 60° C., 2 weeks | Poor | Poor |
| | Stability with time cycle (−5 to 40° C.) 2 weeks | Poor | Good |

The results of Tables 1 and 2 revealed that Component (E): polyhydric alcohol is indispensable to ensure the superior emulsification stability of an O/W composition containing AMP and having a high viscosity under high temperature or during storage under varied temperatures. In addition to polyhydric alcohol, the O/W composition is required to contain Component (F): glycerin fatty acid ester. A superior effect can be obtained when using a self-emulsifiable glycerin fatty acid ester.

Prescription Example

An O/W emulsion composition was prepared according to the method described in the Examples using the components in the proportions of Table 3. The unit shows a proportion based on the total weight of the final emulsion composition (100 wt. %).

TABLE 3

| | | Wt. % |
|---|---|---|
| 1 | Adenosine monophosphate disodium | 1.0 |
| 2 | Self-emulsifiable glycerin fatty acid ester | 1.2 |
| 3 | Decaglyceryl monomyristate | 1.5 |
| 4 | Hydrogenated soybean phospholipid | 0.1 |
| 5 | Stearyl alcohol | 2.0 |
| 6 | Liquid paraffin | 10.0 |
| 7 | Tri(caprylic/capric acid)glyceryl | 5.0 |
| 8 | Methyl polysiloxane | 1.5 |
| 9 | Concentrated glycerin | 10.0 |
| 10 | Acrylic acid-alkyl methacrylate copolymer | 0.15 |
| 11 | pH adjuster | q.s. |
| 12 | Antiseptic | q.s. |
| 13 | Purified water | remainder |

The creamy O/W emulsion composition thus prepared ensured stability with time and a superior feel in use.

The invention claimed is:

1. A creamy O/W emulsion composition containing the following Components (A) to (F) and (H) at the following proportions based on its total amount, wherein the viscosity of the emulsion composition at 20° C. is 5000 to 60000 cps:
    (A) not less than 0.1 wt. % of adenosine phosphate ester selected from at least one member selected from the group consisting of cyclic adenosine 3',5'-monophosphate, adenosine monophosphate, adenosine diphosphate, adenosine triphosphate, and salts thereof;
    (B) 0.5 to 6 wt. % of polyglycerin fatty acid ester;
    (C) 0.05 to 0.7 wt. % of acrylic acid-alkyl methacrylate copolymer;
    (D) 0.5 to 10 wt. % of amphiphilic lipid selected from at least one member selected from the group consisting of higher fatty acids (C14-22), higher alcohols (C8-22), mono alkyl glyceryl ethers (alkyl carbon number=8 to 22), ceramides, ceramide saccharides, sugar lipids, lecithins and lecithin derivatives;
    (E) 0.5 to 20 wt. % of polyhydric alcohol;
    (F) 0.3 to 5 wt. % of self-emulsifiable glycerin fatty acid ester having a nonionic surface-activation effect obtained by mixing a hydrophilic surfactant with a monoglycerin fatty acid ester; and
    (H) 10 to 30 wt. % of oil.

2. The creamy O/W emulsion composition according to claim 1, wherein Component (B) is an ester of a $C_{12-36}$ fatty acid and a polyglycerin having a polymerization degree of 6 or more.

3. The creamy O/W emulsion composition according to claim 1 or 2, wherein Component (C) has a $C_{5-40}$ alkyl group.

4. The creamy O/W emulsion composition according to claim 1, wherein Component (E) is a trihydric alcohol.

5. The creamy O/W emulsion composition according to claim 1, further comprising (G) water in a proportion of 30 to 80 wt. %.

6. The creamy O/W emulsion composition according to claim 1, wherein the creamy O/W emulsion composition is a skin cosmetic, an externally-applied medicinal product for the skin, or a quasi drug for the skin.

7. A method for producing a creamy O/W emulsion composition containing the following Components (A) to (F) and (H) at the following proportions based on its total amount, wherein the viscosity of the emulsion composition at 20° C. is 5000 to 60000 cps:
   (A) not less than 0.1 wt. % of adenosine phosphate ester;
   (B) 0.5 to 6 wt. % of polyglycerin fatty acid ester;
   (C) 0.05 to 0.7 wt. % of acrylic acid-alkyl methacrylate copolymer;
   (D) 0.5 to 10 wt. % of amphiphilic lipid selected from at least one member selected from the group consisting of higher fatty acids (C14-22), higher alcohols (C8-22), mono alkyl glyceryl ethers (alkyl carbon number=8 to 22), ceramides, ceramide saccharides, sugar lipids, lecithins and lecithin derivatives;
   (E) 0.5 to 20 wt. % of polyhydric alcohol;
   (F) 0.3 to 5 wt. % of self-emulsifiable glycerin fatty acid ester having a nonionic surface-activation effect obtained by mixing a hydrophilic surfactant with a monoglycerin fatty acid ester; and
   (H) 10 to 30 wt. % of oil,
   the method comprising the steps of:
   1) preparing a non-aqueous emulsion using a composition containing (B) polyglycerin fatty acid ester, (D) amphiphilic lipid, (E) polyhydric alcohol, (F) self-emulsifiable glycerin fatty acid ester; and (H) oil;
   2) preparing an aqueous solution containing (A) at least one adenosine phosphate ester selected from the group consisting of cyclic adenosine 3'5'-monophosphate, adenosine monophosphate, adenosine diphosphate, adenosine triphosphate, and salts thereof, and (C) acrylic acid-alkyl methacrylate copolymer; and
   3) mixing the non-aqueous emulsion and the aqueous solution under heat to produce an emulsion.

8. An emulsion stabilization method for an adenosine-phosphate-ester-containing creamy O/W emulsion composition containing the following Components (A) to (F) and (H) at the following proportions based on its total amount, wherein the viscosity of the emulsion composition at 20° C. is 5000 to 60000 cps:
   (A) not less than 0.1 wt. % of adenosine phosphate ester;
   (B) 0.5 to 6 wt. % of polyglycerin fatty acid ester;
   (C) 0.05 to 0.7 wt. % of acrylic acid-alkyl methacrylate copolymer;
   (D) 0.5 to 10 wt. % of amphiphilic lipid selected from at least one member selected from the group consisting of higher fatty acids (C14-22), higher alcohols (C8-22), mono alkyl glyceryl ethers (alkyl carbon number=8 to 22), ceramides, ceramide saccharides, sugar lipids, lecithins and lecithin derivatives;
   (E) 0.5 to 20 wt. % of polyhydric alcohol;
   (F) 0.3 to 5 wt. % of self-emulsifiable glycerin fatty acid ester having a nonionic surface-activation effect obtained by mixing a hydrophilic surfactant with a monoglycerin fatty acid ester; and
   (H) 10 to 30 wt. % of oil,
   the method comprising the steps of:
   1) preparing a non-aqueous emulsion using a composition containing (B) polyglycerin fatty acid ester, (D) amphiphilic lipid, (E) polyhydric alcohol, (F) self-emulsifiable glycerin fatty acid ester; and (H) oil;
   2) preparing an aqueous solution containing (A) at least one adenosine phosphate ester selected from the group consisting of cyclic adenosine 3'5'-monophosphate, adenosine monophosphate, adenosine diphosphate, adenosine triphosphate, and salts thereof, and (C) acrylic acid-alkyl methacrylate copolymer; and
   3) mixing the non-aqueous emulsion and the aqueous solution under heat to produce an emulsion.

9. The creamy O/W emulsion composition according to claim 1, wherein the viscosity of the emulsion composition at 20° C. is 20000 to 30000 cps.

* * * * *